(12) United States Patent
Sanders

(10) Patent No.: US 8,628,781 B2
(45) Date of Patent: Jan. 14, 2014

(54) PREVENTION AND TREATMENT OF CAST NEPHROPATHY

(75) Inventor: Paul W. Sanders, Birmingham, AL (US)

(73) Assignees: The UAB Research Foundation, Birmingham, AL (US); The United States of America, as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 13/639,002

(22) PCT Filed: Apr. 1, 2011

(86) PCT No.: PCT/US2011/031005
§ 371 (c)(1),
(2), (4) Date: Nov. 6, 2012

(87) PCT Pub. No.: WO2011/123826
PCT Pub. Date: Oct. 6, 2011

(65) Prior Publication Data
US 2013/0129714 A1    May 23, 2013

Related U.S. Application Data

(60) Provisional application No. 61/320,344, filed on Apr. 2, 2010.

(51) Int. Cl.
| | | |
|---|---|---|
| *A61K 39/00* | (2006.01) | |
| *A61K 38/00* | (2006.01) | |
| *A61K 38/10* | (2006.01) | |
| *A61K 38/12* | (2006.01) | |
| *A61K 38/04* | (2006.01) | |

(52) U.S. Cl.
USPC ......... 424/185.1; 530/317; 530/326; 530/327

(58) Field of Classification Search
None
See application file for complete search history.

(56) References Cited

U.S. PATENT DOCUMENTS

| | | |
|---|---|---|
| 2006/0140945 A1 | 6/2006 | Inada et al. |
| 2007/0251882 A1 | 11/2007 | Bradwell et al. |
| 2009/0203603 A1 | 8/2009 | Baron et al. |

OTHER PUBLICATIONS

Davies, John S., The Cyclization of Peptides and Depsipeptides. J. Peptide Sci., 9:471-501 (2003).
Estojak, J, Brent, R & Golemis, EA: Correlation of two-hybrid affinity data with in vitro measurements. Mol. Cell. Bioi., 15: 5820-5829, 1995.
Fields, S & Song, 0: A novel genetic system to detect protein-protein interactions. Nature, 340: 245-246, 1989.
Huang, Z-Q, Kirk, KA, Connelly, KG & Sanders, PW: Bence Jones proteins bind to a common peptide segment of Tamm-Horsfall glycoprotein to promote heterotypic aggregation. J. Clin. Invest., 92: 2975-2983, 1993.
Huang, Z-Q & Sanders, PW: Localization of a single binding site for immunoglobulin light chains on human Tamm-Horsfall glycoprotein. J. Clin. Invest., 99: 732-736, 1997.
Lambert, et al., The Interaction of Tamm-Horsfall Protein with the Extracellular Matrix. Immunology, 79:203-210 1993.
Ying, W-Z & Sanders, PW: Mapping the binding domain of immunoglobulin light chains for Tamm-Horsfall protein. Am. J. Pathol., 158: 1859-1866, 2001.
International Preliminary Report on Patentability dated Oct. 2, 2012 for International Application No. PCT/US2011/031005.
Sanders et al., Power Point presentation entitled "Monoclonal Free Light Chains and Renal Damage" presented at the 5th International Symposium on Clinical Applications of Serum Free Light Chain Analysis, Bath UK, Sep. 18, 2008.
Montseny et al., Long-Term Outcome According to Renal Histological Lesions in 118 Patients with Monoclonal Gammopathies. Nep. Dial Trans., 13:1438-1445 1998.
Sanders et al., Pathobiology of Cast Nephropathy from Human Bence Jones Proteins. J. Clin. Invest., 89:630-639 1992.
Wang et al., Immunoglobulin Light Chains Generate Hydrogen Peroxide. Am. Soc. Neph. 18:1239-1245 2007.
Jovine et al., The ZP Domain is a Conserved Module for Polymerization of Extracellular Proteins. Nat. Cell Bio. 4:457-461 2002.
Dimopolous et al. "Pathogenesis and treatment of renal failure in multiple myeloma," Leukemia 22(8): 1485-93 (2008).
International Search Report dated Dec. 27, 2011 for International Application No. PCT/US2011/031005.

*Primary Examiner* — Phuong Huynh
(74) *Attorney, Agent, or Firm* — Kilpatrick, Townsend & Stockton LLP

(57) ABSTRACT

Provided herein are polypeptides comprising or consisting essentially of a QSYDNTLSGSYVF (SEQ ID NO:1) or LSADSSGSYLYVF (SEQ ID NO:2) amino acid sequence. Also provided herein are methods of treating or preventing cast nephropathy in a subject. The methods comprise identifying a subject with or at risk of developing cast nephropathy and administering to the subject any of the polypeptides disclosed herein.

4 Claims, 4 Drawing Sheets

SEQUENCE LISTING

```
<160> NUMBER OF SEQ ID NOS: 34

<210> SEQ ID NO 1
<211> LENGTH: 13
<212> TYPE: PRT
<213> ORGANISM: Artificial Sequence
<220> FEATURE:
<223> OTHER INFORMATION: Synthetic Construct

<400> SEQUENCE: 1

Gln Ser Tyr Asp Asn Thr Leu Ser Gly Ser Tyr Val Phe
1               5                   10
```

```
<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Leu Ser Ala Asp Ser Ser Gly Ser Tyr Leu Tyr Val Phe
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Met Gln Gly Thr His Trp Pro Pro Leu Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gln Val Trp Asp Ser Thr Ser Asp His Tyr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

<400> SEQUENCE: 5

Gln Ser Tyr Asp Asn Thr Leu Ser Gly Ser Tyr Val
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Val Trp Asp Asn Ser Val Gly Val
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Gln Val Trp His Ser Ser Ser Asp His Tyr Val
1               5                   10
```

```
<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Gln Ser Ala Asp Asn Ser Gly Thr Phe Trp Ile
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Construct

<400> SEQUENCE: 9

Gln Ser Ala Asp Ser Ser Gly Thr Tyr Trp Val
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Leu Ser Ala Asp Ser Ser Gly Ser Tyr Leu Tyr Val
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Tyr Ser Ala Thr Asp Asn Asn Trp Val
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Gln Ser Thr Asp Ser Ser Gly Thr Tyr Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Gln Ala Trp Asp Arg Ser Thr Val Val
1               5

<210> SEQ ID NO 14
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 14

Glu Thr Trp Asp Ser Asp Thr Arg Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Gln Thr Trp Asp Thr Gly Phe Trp Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

Ala Met Trp Tyr Ser Asp Val Tyr Val
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Met Ile Arg Gly Ile
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Leu Ile Trp His Ser Arg Ala Tyr Val
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic Construct

<400> SEQUENCE: 19

Val Ser Leu Met Met Ala Gly Ile Met Ser
1               5                   10

<210> SEQ ID NO 20
<211> LENGTH: 9
<212> TYPE: PRT
<213> ORGANISM: Artificial Sequence
```

```
<220> FEATURE:
<223> OTHER INFORMATION: Synthetic Construct

<400> SEQUENCE: 20

Gln Ser Ser Asp Thr Thr Asn Gln Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gln Gln Tyr Tyr Ser Ala Pro Pro Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Tyr Gly Ser Ser Pro Cys Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Leu Asn Ser Tyr Pro Phe Thr
1               5

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Trp Tyr Gln Gln Lys Ala Gly Ser Pro Pro Gln His Leu Leu Thr
1               5                   10                  15

<210> SEQ ID NO 25
<211> LENGTH: 34
<212> TYPE: PRT
<213> ORGANISM: Artificial Sequence
<220> FEATURE:
<223> OTHER INFORMATION: Synthetic Construct

<400> SEQUENCE: 25

Gly Val Pro Ser Arg Phe Ser Gly Ser Lys Asp Ala Ser Ala Asn Ala
1               5                   10                  15

Gly Ile Leu Leu Ile Ser Gly Leu His Ser Glu Asp Glu Ala Asp Asn
                20                  25                  30

Asp Cys

<210> SEQ ID NO 26
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Ala His Trp Ser Gly His Cys Cys Leu
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Gln Val Trp His Ser Ser Ser Asp His Tyr Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Gln Val Trp Asp Ser Thr Ser Asp His Tyr Val
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic Construct

<400> SEQUENCE: 29

Leu Ser Ala Phe Ser Phe Gly Phe Tyr Leu Tyr Val
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Leu Ser Ala Phe Ser Phe Gly Ser Tyr Leu Tyr Val
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Leu Ser Ala Phe Ser Ser Gly Ser Tyr Leu Tyr Val
1               5                   10

<210> SEQ ID NO 32
<211> LENGTH: 14
<212> TYPE: PRT
```

```
-continued

<213> ORGANISM: Artificial Sequence
<220> FEATURE:
<223> OTHER INFORMATION: Synthetic Construct

<400> SEQUENCE: 32

Cys Leu Ser Ala Asp Ser Ser Gly Ser Tyr Leu Tyr Val Cys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Cys Leu Ser Ala Phe Ser Phe Gly Phe Tyr Leu Tyr Val Cys
1               5                   10

<210> SEQ ID NO 34
<211> LENGTH: 76
<212> TYPE: DNA
<213> ORGANISM: Artificial Sequence
<220> FEATURE:
<223> OTHER INFORMATION: Synthetic Construct

<400> SEQUENCE: 34
agtgaattcc ctccccagca tctcctgacg caccccgggt gtgggatcca tggagtcccc      60
agccgcttcc ctgcag                                                      76
```

PREVENTION AND TREATMENT OF CAST NEPHROPATHY

CROSS REFERENCE TO RELATED APPLICATIONS

This application claims the benefit of U.S. Provisional Application No. 61/320,344, filed on Apr. 2, 2010, which is incorporated by reference herein in its entirety.

REFERENCE TO SEQUENCE LISTING

The Sequence Listing submitted Oct. 2, 2012, as a text file named "10030_131US1_2012_10_02_Sequence_Listing.txt," created on Oct. 2, 2012 and having a size of 7,499 bytes is hereby incorporated by reference pursuant to 37 C.F.R. §1.52(e)(5).

BACKGROUND

Cast nephropathy, or myeloma kidney, is an inflammatory tubulointerstitial renal lesion that occurs in the setting of multiple myeloma. Characteristically, multiple intraluminal proteinaceous casts are identified mainly in the distal portion of the nephrons. The casts are typically acellular, homogenous and eosinophilic with multiple fracture lines. Immunofluorescence and immunoelectron microscopy confirm that the casts contain light chain immunoglobulins and Tamm-Horsfall glycoprotein. Glomeruli are usually normal in appearance. Casts obstruct the flow of tubular fluid, producing obstruction and the clinical manifestations of renal failure. Persistence of the casts produces inflammation and tubular atrophy that typify myeloma kidney. The end result is end-stage kidney failure. Renal failure from this lesion may present acutely or as a chronic progressive disease and may develop at any stage of myeloma.

SUMMARY

Provided herein are polypeptides comprising or consisting essentially of a QSYDNTLSGSYVF (SEQ ID NO:1) or LSADSSGSYLYVF (SEQ ID NO:2) amino acid sequence, optionally in cyclized form. Further provided are compositions comprising the polypeptides.

Also provided herein are methods of treating or preventing cast nephropathy in a subject. The methods can comprise identifying a subject with or at risk of developing cast nephropathy and administering to the subject any of the polypeptides or compositions provided herein. The polypeptide or composition inhibits binding of a light chain immunoglobulin to a Tamm-Horsfall protein (THP).

The methods can comprise identifying a subject with or at risk of developing cast nephropathy and administering to the subject an antibody or fragment thereof that inhibits the binding of the light chain immunoglobulin to a Tamm-Horsfall protein (THP).

The methods can also comprise identifying a subject with or at risk of developing cast nephropathy and administering to the subject a nucleic acid sequence that inhibits binding of a light chain immunoglobulin to a Tamm-Horsfall protein.

DESCRIPTION OF DRAWINGS

FIG. 3A shows a portion of the vector (SEQ ID NO:34) engineered to test the interactions of the CDR3 domain with the Tamm-Horsfall protein. Addition of the framework regions permits each CDR3, which was ligated into the construct using Sma1 and BamH1, to achieve proper folding into a loop structure. FIG. 3B is a histogram demonstrating that sequences capable of forming a loop structure were capable of binding the Tamm-Horsfall protein. The sequences that were predicted to not form loop structures, LKBPLL53 (SEQ ID NO:17) and ITPBLL2 (SEQ ID NO:27), did not interact with the Tamm-Horsfall protein. The CDR3 domain of ITPBLL2 differed from the CDR3 domain of ITPBLL1 (SEQ ID NO:28) by only two amino acids (underlined), which were sufficient to inhibit formation of a loop structure, and, thus, binding to the Tamm-Horsfall protein. Other sequences capable of binding the Tamm-Horsfall protein were the ITPBLL86 (SEQ ID NO:10) and ITPBLL69 (SEQ ID NO:16) sequences. N=6 experiments for each group.

DETAILED DESCRIPTION

Figure 1:
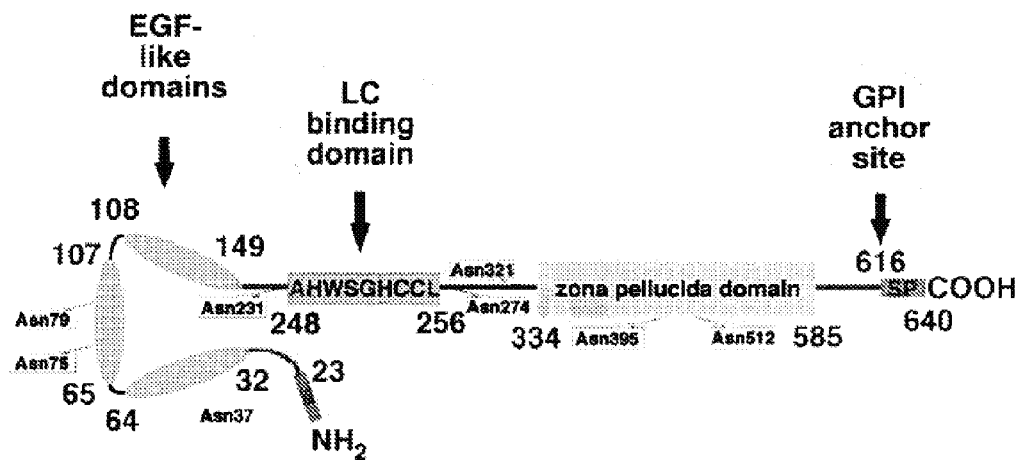
FIG. 1 shows a schematic of the Tamm-Horsfall protein (THP). Shown in the schematic are the epidermal growth factor (EGF)-like domains, the immunoglobulin light chain (LC) binding domain (SEQ ID NO:26), and the glycosylphosphatidylinisotol (GPI) anchor site.
Figure 2:
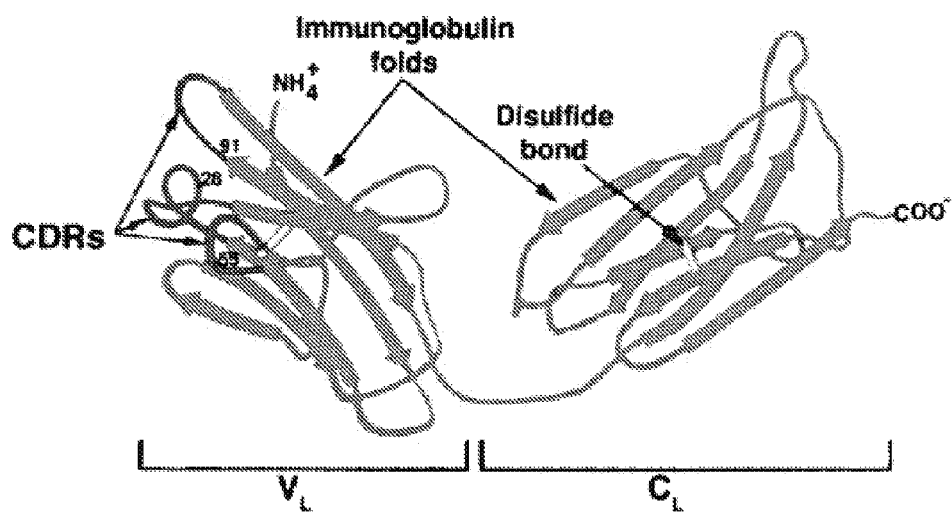
FIG. 2 shows a schematic of the variable ($V_L$) and constant ($C_L$) regions of a free immunoglobulin light chain. Shown in the schematic are the complementary determining regions (CDRs), the immunoglobulin folds, and a disulfide bond.

Intravenous infusion of nephrotoxic human light chains in rats elevates proximal tubule pressure and simultaneously decreases single nephron glomerular filtration rate; intraluminal protein casts can be identified in these kidneys. Myeloma casts contain Tamm-Horsfall protein (FIG. 1) and occur initially in the distal nephron, which provides an optimum environment for precipitation of light chains. Casts occur primarily because light chains coaggregate with Tamm-Horsfall protein. Tamm-Horsfall protein, which is synthesized exclusively by cells of the thick ascending limb of the loop of Henle, comprises the major fraction of total urinary protein in healthy individuals and is the predominant constituent of urinary casts.

Cast-forming immunoglobulin light chains, also referred to as Bence Jones proteins, bind to the same site on the peptide backbone of the Tamm-Horsfall protein; binding results in coaggregation of these proteins and subsequent occlusion of the tubule lumen by the precipitated protein complexes. Intranephronal obstruction and renal failure ensue. Immunoglobulin light chains that bind to Tamm-Horsfall protein are potentially nephrotoxic.

Coaggregation of Tamm-Horsfall protein with immunoglobulin light chains also depends upon the ionic environment and the physiochemical properties of the light chain, and not all patients with myeloma develop cast nephropathy, even when the urinary excretion of immunoglobulin light chains is very high. Increasing concentrations of sodium chloride or calcium, but not magnesium, facilitate coaggregation. Conditions that further reduce flow rates, such as volume depletion, can accelerate tubule obstruction or convert non-toxic light chains into cast-forming proteins. Volume depletion and hypercalcemia are recognized factors that promote acute renal failure from cast nephropathy.

Provided are polypeptides comprising or consisting essentially of a QSYDNTLSGSYVF (SEQ ID NO:1) or a LSADSSGSYLYVF (SEQ ID NO:2) amino acid sequence. Optionally, the polypeptide is cyclized or is contained in a composition. As an example, the polypeptide can further comprise a first cysteine residue at a carboxy-terminal end and a second cysteine residue at an amino-terminal end of the polypeptide. The cysteine residues allow cyclization by an SH-linkage.

Also provided herein are methods of treating or preventing cast nephropathy in a subject. The methods comprise identifying a subject with or at risk of developing cast nephropathy and administering to the subject any of the polypeptides or compositions disclosed herein. The polypeptide or composition inhibits the binding of the light chain immunoglobulin to a Tamm-Horsfall protein. The composition can, for example, comprise a polypeptide consisting essentially of a QSYDNTLSGSYVF (SEQ ID NO:1) or a LSADSSGSYLYVF (SEQ ID NO:2) amino acid sequence. Optionally, the polypeptides comprise a cysteine residue at both ends.

By way of example, the methods comprise identifying a subject with or at risk of developing cast nephropathy and administering to the subject an antibody or a fragment thereof that inhibits the binding of the light chain immunoglobulin to a Tamm-Horsfall protein (THP). Optionally, the antibody or fragment thereof binds a CDR3 of the light chain immunoglobulin. The CDR3 of the light chain immunoglobulin can, for example, comprise an amino acid sequence selected from the group consisting of MQGTHWPPLT (SEQ ID NO:3), QVWDSTSDHY (SEQ ID NO:4), QSYDNTLSGSYV (SEQ ID NO:5), QVWDNSVGV (SEQ ID NO:6), QVWHSSSDHYV (SEQ ID NO:7), QSADNSGTFWI (SEQ ID NO:8), QSADSSGTYWV (SEQ ID NO:9), LSADSSGSYLYV (SEQ ID NO:10), YSATDNNWV (SEQ ID NO:11); QSTDSSGTYR (SEQ ID NO:12), QAWDRSTVV (SEQ ID NO:13), ETWDSDTRV (SEQ ID NO:14), QTWDTGFWV (SEQ ID NO:15), AMWYSDVYV (SEQ ID NO:16), MIRGI (SEQ ID NO:17), LIWHSRAYV (SEQ ID NO:18), VSLMMAGIMS (SEQ ID NO:19), QSSDTTNQV (SEQ ID NO:20), QQYYSAPPT (SEQ ID NO:21), QQYGSSPCT (SEQ ID NO:22), and QQLNSYPFT (SEQ ID NO:23).

The methods can comprise identifying a subject with or at risk of developing cast nephropathy and administering to the subject a nucleic acid sequence that inhibits the binding of a light chain immunoglobulin to a Tamm-Horsfall protein (THP). Optionally, the nucleic acid sequence is a vector comprising a first nucleic acid sequence encoding a polypeptide that inhibits the binding of the light chain immunoglobulin to the THP. The vector can, for example, comprise a second and third nucleic acid sequence, wherein each of the second and third nucleic acid sequences encode a light chain immunoglobulin framework fragment, and wherein the second and third nucleic acid sequences flank the first nucleic acid sequence. Optionally, at least one of the light chain immunoglobulin framework fragments comprises a WYQQKAGSPPQHLLT (SEQ ID NO:24) or a GVPSRFSGSKDASANAGILLISGLHSEDEADNDC (SEQ ID NO:25) amino acid sequence. The encoded polypeptide that inhibits the binding of the light chain immunoglobulin to the THP can, for example, form a loop structure. Optionally, the encoded polypeptide comprises a QSYDNTLSGSYVF (SEQ ID NO:1) or a LSADSSGSYLYVF (SEQ ID NO:2) amino acid sequence.

Optionally, the nucleic acid sequence is an inhibitory nucleic acid sequence. The inhibitory nucleic acid molecule can, for example be selected from the group consisting of a microRNA (miRNA) molecule, a short interfering RNA (siRNA) molecule, and an antisense molecule. Optionally, the inhibitory nucleic acid molecule inhibits the expression of the Tamm-Horsfall protein (THP), thereby indirectly decreasing binding of the light chain immunoglobulin to THP. Optionally, the inhibitory nucleic acid molecule inhibits the expression of the light chain immunoglobulins binding to the Tamm-Horsfall protein, thereby indirectly decreasing binding of the light chain immunoglobulin to THP.

As used herein, an inhibitory nucleic acid sequence can be a short-interfering RNA (siRNA) sequence or a micro-RNA (miRNA) sequence. A 21-25 nucleotide siRNA or miRNA sequence can, for example, be produced from an expression vector by transcription of a short-hairpin RNA (shRNA) sequence, a 60-80 nucleotide precursor sequence, which is subsequently processed by the cellular RNAi machinery to produce either a siRNA or miRNA sequence. Alternatively, a 21-25 nucleotide siRNA or miRNA sequence can, for example, be synthesized chemically. Chemical synthesis of specific siRNA or miRNA molecules is commercially available from such corporations as Dharmacon, Inc. (Lafayette, Colo.), Qiagen (Valencia, Calif.), and Ambion (Austin, Tex.). An siRNA sequence preferably binds a unique sequence within the Tamm Horsfall or light immunoglobulin chain mRNA with exact complementarity and results in the degradation of the mRNA molecule. A miRNA sequence preferably binds a unique sequence within the Tamm Horsfall or light immunoglobulin chain mRNA with exact or less than exact complementarity and results in the translational repression of the mRNA molecule. A miRNA sequence can bind anywhere within the mRNA sequence but preferably binds within the 3' untranslated region of the mRNA molecule. Methods of delivering siRNA or miRNA molecules are known in the art. See, e.g., Oh and Park, Adv. Drug. Deliv. Rev. 61(10):850-62 (2009); Gondi and Rao, J. Cell Physiol. 220(2):285-91 (2009); and Whitehead et al., Nat. Rev. Drug. Discov. 8(2):129-38 (2009).

As used herein, an inhibitory nucleic acid sequence can be an antisense nucleic acid sequence. Antisense nucleic acid sequences can, for example, be transcribed from an expression vector to produce an RNA which is complementary to at least a unique portion of the Tamm Horsfall or light immunoglobulin chain mRNA and/or the endogenous gene which encodes the Tamm Horsfall protein or light immunoglobulin chain. Hybridization of an antisense nucleic acid under specific cellular conditions results in inhibition of protein expression by inhibiting transcription and/or translation.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

The polypeptides provided herein, including fragments, have a desired function. The polypeptides as described herein selectively inhibit the binding of light chain immunoglobulins with the Tamm Horsfall protein. The polypeptides are tested for their desired activity using the in vitro assays described herein, or by analogous methods. Optionally, their therapeutic, diagnostic or other purification activities are tested according to known testing methods.

As with all peptides, polypeptides, and proteins, including fragments thereof, it is understood that additional modifications in the amino acid sequence of the polypeptides can occur that do not alter the nature or function of the peptides, polypeptides, or proteins. Such modifications include conservative amino acid substitutions and are discussed in greater detail below. The polypeptides described herein can include, for example, 1 or 2 conservative substitutions so long as the modified polypeptides block binding between the light chain immunoglobulins and the Tamm Horsfall protein.

The polypeptides described herein can be further modified so long as the desired function is maintained. It is understood that one way to define any known modifications and derivatives or those that might arise, of the disclosed nucleic acids and proteins herein is through defining the modifications and derivatives in terms of identity to specific known sequences. Specifically disclosed are polypeptides which have at least 95, 96, 97, 98, or 99 percent identity to the polypeptides provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183: 281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and are disclosed herein.

Protein modifications include amino acid sequence modifications. Modifications in amino acid sequence may arise naturally as allelic variations (e.g., due to genetic polymorphism) or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Post-translational modifications can include variations in the type or amount of carbohydrate moieties of the protein core or any fragment or derivative thereof Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods including the methods described in the Examples below. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example, M13 primer mutagenesis and PCR mutagenesis.

Antibodies described herein bind the CDR3 of the light chain immunoglobulins that bind the Tamm Horsfall protein (THP) and inhibit the binding of the light chain immunoglobulin to the Tamm Horsfall protein. Optionally, the antibodies described herein bind THP at an amino acid sequence comprising AHWSGHCCL (SEQ ID NO:26). The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77, 1985) and by Boerner et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362:255-8 (1993); Bruggermann et al., Year in Immunol. 7:33 (1993)). Antigens, such as the amino acid sequence of any of SEQ ID NOs:4-23 or SEQ ID NO:32 can be used, in various methods, to stimulate antibody production.

As used herein, the term antibody encompasses, but is not limited to, whole immunoglobulin (i.e., an intact antibody) of any class. Antibodies are usually heterotetrameric glycoproteins, composed of two identical light (L) chains and two identical heavy (H) chains. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain.

The term variable is used herein to describe certain portions of the antibody domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR).

As used herein, the term epitope is meant to include any determinant capable of specific interaction with the provided antibodies. Epitopic determinants usually consist of chemically active surface groupings of molecules such as amino acids or sugar side chains and usually have specific three dimensional structural characteristics, as well as specific charge characteristics.

The term antibody or fragments thereof can also encompass chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain binding activity are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York (1988)).

Also included within the meaning of antibody or fragments thereof are conjugates of antibody fragments and antigen binding proteins (single chain antibodies) as described, for example, in U.S. Pat. No. 4,704,692, the contents of which are hereby incorporated by reference in their entirety.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies, A Laboratory Manual. Cold Spring Harbor Publications, New York (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent can be the amino acid sequences of the CDR3s from the light chain immunoglobulins that bind the Tamm-Horsfall protein, the amino acid sequence of the Tamm-Horsfall protein where the CDR3 binds, or an immunogenic fragment thereof.

Generally, either peripheral blood lymphocytes (PBLs) are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium") substances that prevent the growth of HGPRT-deficient cells.

The culture medium in which the hybridoma cells are cultured can then be assayed for the presence of monoclonal antibodies directed against the CDR3 of the light chain immunoglobulins that bind the Tamm-Horsfall protein, the Tamm-Horsfall protein, or selected epitopes thereof, including, for example, a polypeptide comprising any of SEQ ID NOs:4-23 or SEQ ID NO:26. The antibodies are screened for the ability to block binding between the CDR3 of the light chain immunoglobulin and the Tamm Horsfall protein. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art, and are described further in Harlow and Lane Antibodies, A Laboratory Manual, Cold Spring Harbor Publications, New York (1988).

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for the CDR3 of the light chain immunoglobulin that binds the Tamm Horsfall protein or the Tamm Horsfall protein and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

One method of producing proteins comprising the provided antibodies or polypeptides is to link two or more amino acids, peptides, or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry (Applied Biosystems, Inc.; Foster City, Calif.). A peptide or polypeptide can be synthesized and not cleaved from its synthesis resin whereas the other fragment of peptide or polypeptide can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form a peptide, polypeptide, an antibody, or fragment thereof (Grant G A (1992) Synthetic Peptides: A User Guide. W.H. Freeman and Co., N.Y. (1992); Bodansky and Trost, Ed. (1993) Principles of Peptide Synthesis. Springer Verlag Inc., NY). Alternatively, the peptide or polypeptide can by independently synthesized in vivo. Once isolated, these independent peptides or polypeptides may also be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776 779 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a polypeptide is illustrated by the preparation of human interleukin 8 (IL-8) (Baggiolini et al., FEBS Lett. 307:97-101 (1992); Clark et al., J. Biol. Chem. 269:16075 (1994); Clark et al., Biochemistry 30:3128 (1991); Rajarathnam et al., Biochemistry 33:6623-30 (1994)).

Alternatively, unprotected peptide segments can be chemically linked where the bond formed between the peptide segments as a result of the chemical ligation is an unnatural (non peptide) bond (Schnolzer et al., Science 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-267 (1992)).

The provided polypeptide fragments can be recombinant proteins obtained by cloning nucleic acids encoding the polypeptide in an expression system capable of producing the polypeptide fragments thereof, such as a bacterial, adenovirus or baculovirus expression system. For example, one can determine the active domain of an antibody from a specific hybridoma that can cause a biological effect associated with the interaction of the antibody with the CDR3 of the light chain immunoglobulin that binds the Tamm Horsfall protein or the Tamm-Horsfall protein. For example, amino acids found to not contribute to either the activity or the binding specificity or affinity of the antibody or polypeptide can be deleted without a loss in the respective activity.

Provided herein are methods of treating or preventing cast nephropathy in a subject. Such methods optionally include identifying a subject with or at risk of developing cast nephropathy using any method accepted by one of skill in the art, including, for example, the measurement of free light chain immunoglobulins in serum and urine, pathological analysis on renal biopsies, and early signs and symptoms of renal failure or multiple myeloma. Patients with multiple myeloma and light chain overproduction are at risk of developing renal failure from cast nephropathy and may benefit from this renoprotective agent. Such methods also include administering an effective amount of a composition comprising a polypeptide or a nucleic acid molecule. Optionally, the polypeptides or nucleic acid molecules are contained within a pharmaceutical composition.

Provided herein are compositions containing the provided polypeptides and/or nucleic acid molecules and a pharmaceutically acceptable carrier described herein. The herein provided compositions can be designed to be suitable for administration in vitro, in vivo, or both. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in Remington: *The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the agent, e.g., the polypeptide and/or nucleic acid molecule, to humans or other subjects.

The compositions are administered in a number of ways depending on whether local or systemic treatment is desired, and on the area to be treated. Local administration, e.g., during a surgical procedure, can be with use of a bioabsorbent gel or matrix impregnated with the composition or by flooding the surgical site with the composition. The compositions are administered via any of several routes of administration, including intrarenally with low molecule weight proteins (e.g., lysozyme) as carriers or using catheters to specifically deliver compositions to the renal arteries to target the kidney. The compositions can also be administered via any of several other routes, including topically, orally, parenterally, intravenously, intra-articularly, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the nucleic acid molecule or polypeptide is administered by a vector comprising the nucleic acid molecule or a nucleic acid sequence encoding the polypeptide. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., *Retroviruses*, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g., chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1a promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the E. coli lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cast nephropathy). The term patient or subject includes human and veterinary subjects.

A subject at risk of developing a disease or disorder can be genetically predisposed to the disease or disorder, e.g., have a family history or have a mutation in a gene that causes the disease or disorder or show early signs or symptoms of the disease or disorder. In this case, the disease or disorder can be multiple myeloma or cast nephropathy. A subject currently with multiple myeloma is at risk for developing cast nephropathy. Further, a person with multiple myeloma showing early signs of kidney failure is also a candidate for treatment even if a definitive diagnosis of cast nephropathy has not yet been made. In addition, patients with multiple myeloma and light chain overproduction who do not yet show signs of kidney injury may benefit from this renoprotective agent. Finally, there is growing evidence that cast formation through protein binding to Tamm-Horsfall glycoprotein may also play a role in progression of kidney failure in patients who have chronic kidney disease from diseases other than multiple myeloma. These patients may also benefit from administration of this renoprotective agent.

The methods and agents as described herein are useful for both prophylactic and therapeutic treatment. For prophylactic use, a therapeutically effective amount of the agents described herein are administered to a subject prior to onset (e.g., before obvious signs of cast nephropathy) or during early onset (e.g., upon initial signs and symptoms of cast nephropathy). Prophylactic administration can occur for several days to years prior to the manifestation of symptoms of cast nephropathy. Prophylactic administration can be used, for example, in the preventative treatment of subjects diagnosed with a genetic predisposition to cast nephropathy or with multiple myeloma. Therapeutic treatment involves administering to a subject a therapeutically effective amount of the agents described herein after diagnosis or development of cast nephropathy.

According to the methods taught herein, the subject is administered an effective amount of the agent (e.g., composition comprising a polypeptide, an antibody or fragment thereof, or a nucleic acid molecule). The terms effective amount and effective dosage are used interchangeably. The term effective amount is defined as any amount necessary to produce a desired physiologic response (e.g., rapid reduction of light chain immunoglobulins in subject). Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Thus, treatment refers, for example, to an improvement in one or more parameters of kidney function.

As used herein, the terms prevent, preventing, and prevention of a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

In Vitro Studies to Determine Peptides Capable of Inhibiting Light Chain Immunoglobulins Binding with Tamm Horsfall Protein Previous studies have demonstrated that the free immunoglobulin light chains bind to a specific domain on the human Tamm-Horsfall protein, but possess variable affinities for the Tamm-Horsfall protein (Table 2). Table 2 provides the immunoglobulin light chains and their respective CDR3 sequences. The amino acid composition of the CDR3 domain varies among the light chains and determines the affinity of the light chain for the Tamm-Horsfall protein.

TABLE 2

Binding affinities of different light chain immunoglobulins to Tamm-Horsfall protein (THP)

| Light Chain | CDR3 Sequence | Rel. Reactivity |
|---|---|---|
| λ light chain subgroups | | |
| λ1 | | |
| LBPBLL2N | QSYDNTLSGSYV (SEQ ID NO: 5) | 6.7 ± 1.0 |
| λIII | | |
| ITPBLL56 (λIII) | QVWDNSVGV (SEQ ID NO: 6) | 7.1 ± 1.3 |
| ITPBLL2 (λIII) | QVWHSSSDHYV (SEQ ID NO: 7) | 2.0 ± 0.2 |
| LBPBLL2 (λIII) | QSADNSGTFWI (SEQ ID NO: 8) | 6.8 ± 0.8 |
| ITPBLL79 (λIII) | QSADSSGTYWV (SEQ ID NO: 9) | 6.0 ± 2.1 |
| ITPBLL86 (λIIIa) | LSADSSGSYLYV (SEQ ID NO: 10) | 7.8 ± 0.9 |
| LKPBLL68 (λIII) | YSATDNNWV (SEQ ID NO: 11) | 6.3 ± 0.6 |
| ITPBLL11 (IIIb) | QSTDSSGTYR (SEQ ID NO: 12) | 3.4 ± 0.3 |
| ITPBLL22 (λIIIc) | QAWDRSTVV (SEQ ID NO: 13) | 4.9 ± 0.7 |
| λIV | | |
| LBPBL2Q (λIV) | ETWDSDTRV (SEQ ID NO: 14) | 6.5 ± 0.8 |
| ITPBLL68 (λIV) | QTWDTGFWV (SEQ ID NO: 15) | 5.6 ± 1.0 |

TABLE 2-continued

Binding affinities of different light chain immunoglobulins to Tamm-Horsfall protein (THP)

| Light Chain | CDR3 Sequence | Rel. Reactivity |
|---|---|---|
| λV | | |
| ITPBLL69 (λV) | AMWYSDVYV (SEQ ID NO: 16) | 2.0 ± 0.4 |
| LKPBLL53 (λV) | MIRGI (SEQ ID NO: 17) | 1.6 ± 0.4 |
| LBPBLL7 (λV) | LIWHSRAYV (SEQ ID NO: 18) | 2.9 ± 0.4 |
| λVI | | |
| ITPBLL75 (λVI) | VSLMMAGIIMS (SEQ ID NO: 19) | 4.8 ± 0.6 |
| LBPBLL2S (λVI) | QSSDTTNQV (SEQ ID NO: 20 | 5.8 ± 0.8 |
| κ light chain subgroups | | |
| κI | | |
| ITPBL5 (κI) | QQYYSAPPT (SEQ ID NO: 21) | 6.5 ± 0.8 |
| κII | | |
| SSH23 (κII) | MQGTHWPPLT (SEQ ID NO: 3) | 4.9 ± 0.7 |
| ITPBL11 (κII) | QQYGSSPCT (SEQ ID NO: 22) | 3.4 ± 0.7 |
| κIV | | |
| BCSyn9 (κIV) | QQLNSYPFT (SEQ ID NO: 23) | 3.2 ± 1.0 |

The yeast two-hybrid system was employed to determine the site on the immunoglobulin light chain that interacted with the Tamm-Horsfall protein. Using 248- and 787-base pair fragments of the Tamm-Horsfall protein, which contained the previously described immunoglobulin light chain-binding domain, the interaction with unique immunoglobulin light chains that represented a variety of the known isotypes of κ and λ immunoglobulin light chains was examined. A series of truncation mutants of immunoglobulin light chains demonstrated that the CDR3 region of both κ and λ immunoglobulin light chains specifically interacted with these Tamm-Horsfall protein constructs. To confirm these observations, a synthetic peptide (MQGTHWPPLT (SEQ ID NO:3)) that was identical to the CDR3 region of SSH23, a light chain that showed moderate binding affinity, was used in a series of competition studies. This peptide effectively competed with six different immunoglobulin light chains, which had been obtained from patients with myeloma and cast nephropathy, for binding to the Tamm-Horsfall protein. While this was considered an advance, this peptide was not considered to bind avidly enough to the Tamm-Horsfall protein to serve as an effective inhibitor in vivo.

To examine the binding interactions further, the reactions in the yeast two-hybrid analyses were quantified by liquid culture assay of β-galactosidase activity using o-nitrophenyl β-D-galactopyranoside (ONPG; Amersham Life Science, Inc.; Cleveland, Ohio) as the substrate. It has been shown that the relative affinities detected with this reaction correlated with interactions detected using other biochemical methods. While most, but not all, of the immunoglobulin light chains interacted with the Tamm-Horsfall protein, the relative strength of the interactions differed among 21 unique κ and λ immunoglobulin light chains examined. The variable domain of the λVI immunoglobulin light chain, ITPBLL75, showed the lowest affinity interaction: yeast transformed with this construct did not grow in leucine-deficient medium and possessed low β-galactosidase activity. The intact variable region of the λIIIa light chain, ITPBLL86, demonstrated the highest binding affinity among the immunoglobulin light chains tested. Truncation experiments using κ and λ light chains confirmed that the Tamm-Horsfall protein bound specifically to the CDR3 domain of the immunoglobulin light chains. Reactivity with the Tamm-Horsfall protein correlated directly ($R^2=0.2346$; $P=0.02$) with the number of amino acid residues in the CDR3 region.

Figure 3A:
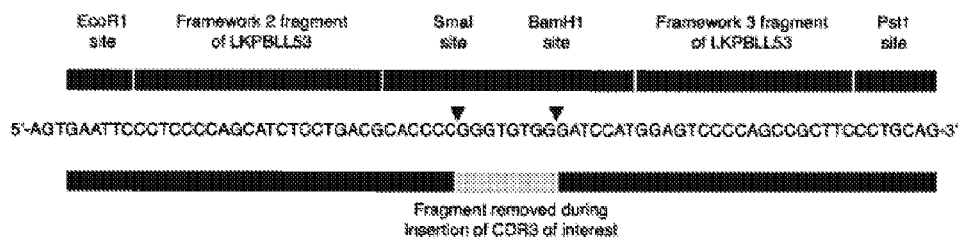
FIGS. 3A and 3B shows that the loop structure of the immunoglobulin light chain is a key determinant in binding efficiency to the Tamm-Horsfall protein.
Figure 3B:
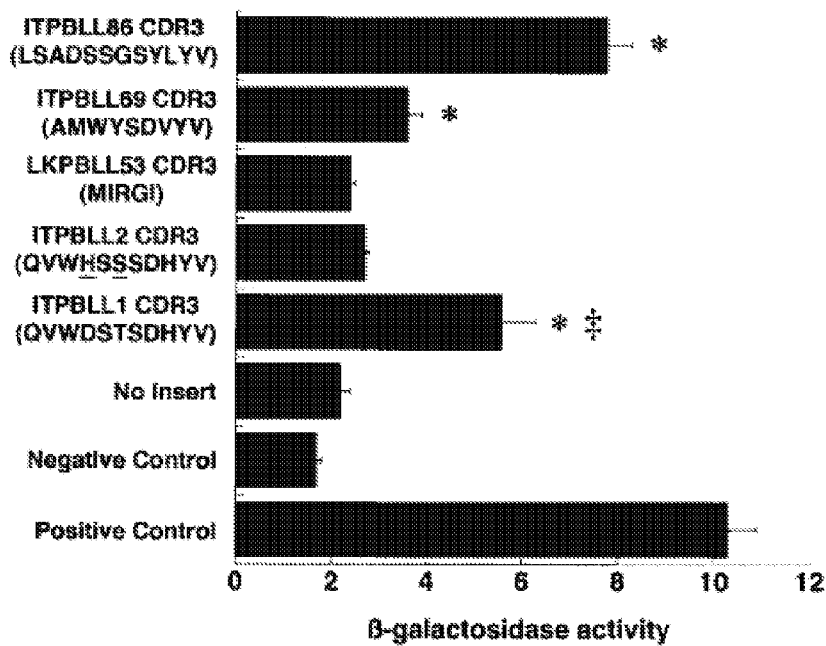

To test the hypothesis that the ability to form a loop structure determined binding affinity, a vector was created that permitted ligation of the CDR3 region of interest between portions of Framework 2 (SEQ ID NO:24) and Framework 3 (SEQ ID NO:25) from a light chain (LKPBLL53) that did not interact with Tamm-Horsfall protein (FIG. 3). The vector that did not contain a CDR3 insert ("no insert") did not interact with the Tamm-Horsfall protein in the yeast two-hybrid assay. Two of the CDR3 regions (from LKPBLL53 and ITPBLL2) that were predicted not to form a loop structure did not interact with the Tamm-Horsfall protein. Among those CDR3 domains that were predicted to form a loop, affinity for the Tamm-Horsfall protein was strong and correlated with that observed using the intact $V_L$ from the parent light chain.

Figure 4:
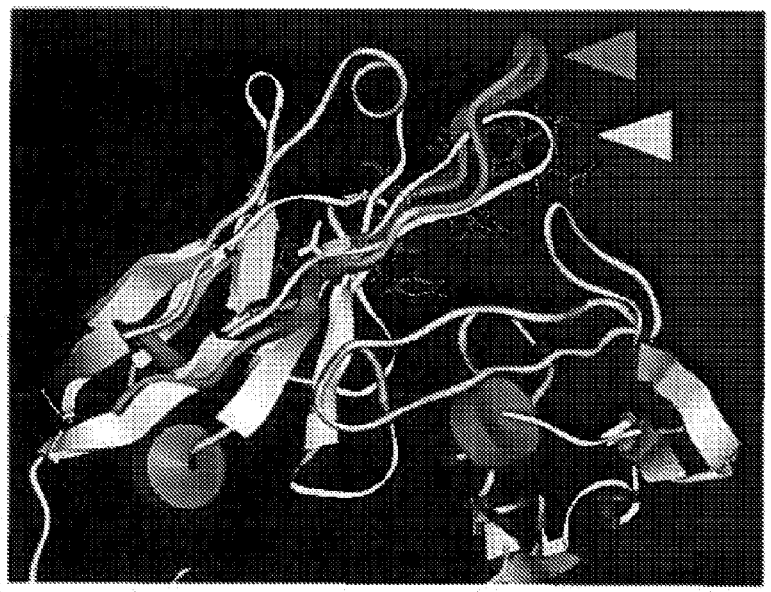
FIG. 4 shows a molecular model of a CDR3 domain (white arrow) on the VL and a superimposed image of the competitor cyclic peptide (grey arrow).
Figure 5:
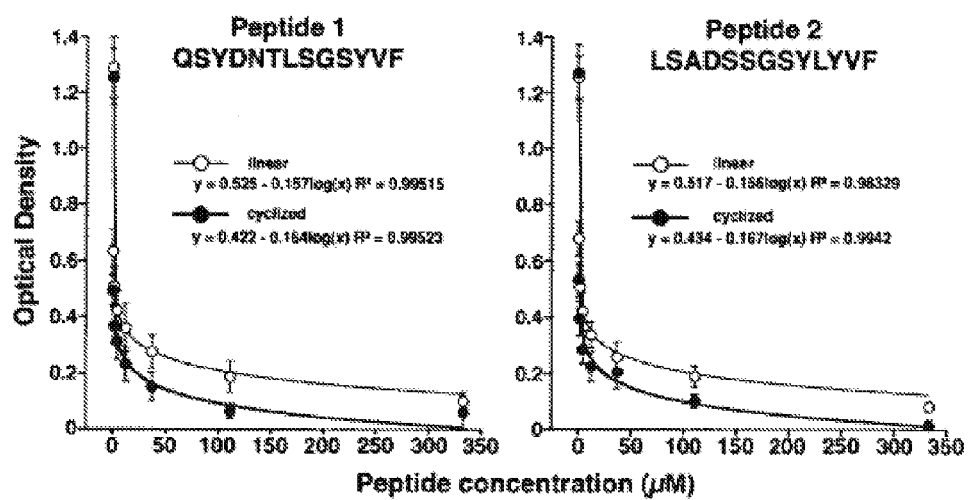
FIG. 5 shows that cyclized peptides inhibit the binding of the immunoglobulin light chain to the Tamm-Horsfall protein to a greater extent than uncyclized peptides. The graphs demonstrate that peptide 1 (QSYDNTLSGSYVF (SEQ ID NO:1)) (left) and peptide 2 (LSADSSGSYLYVF (SEQ ID NO:2)) (right) inhibit binding as an uncyclized peptide and as a cyclized peptide. However, cyclization of the peptides allows greater inhibition at lower concentrations.

Peptides known to react with the Tamm-Horsfall protein in the yeast two-hybrid assay were synthesized, cyclized, and used as inhibitors in a competitive ELISA experiment. The peptides were cyclized by adding cysteine residues to the amino and carboxyl-terminal portions of the peptides and generating an intramolecular disulfide bridge (FIG. 4). Cyclization facilitates formation of the loop structure in solution. Both the linear and cyclized peptides inhibited the binding of the Tamm-Horsfall protein to the immunoglobulin light chains bound in the wells of the microtiter plate, but the efficiency of inhibition was increased by cyclization of the peptide inhibitor. For peptide 1 (QSYDNTLSGSYVF (SEQ ID NO:1)), the $IC_{50}$ fell from 55.0±16.1 nM to 6.7±2.3 nM ($P<0.05$) and for peptide 2 (LSADSSGSYLYVF (SEQ ID NO:2)) the $IC_{50}$ decreased from 90.9±9.1 to 24±4.2 nM ($P<0.05$) (FIG. 5).

Figure 6:
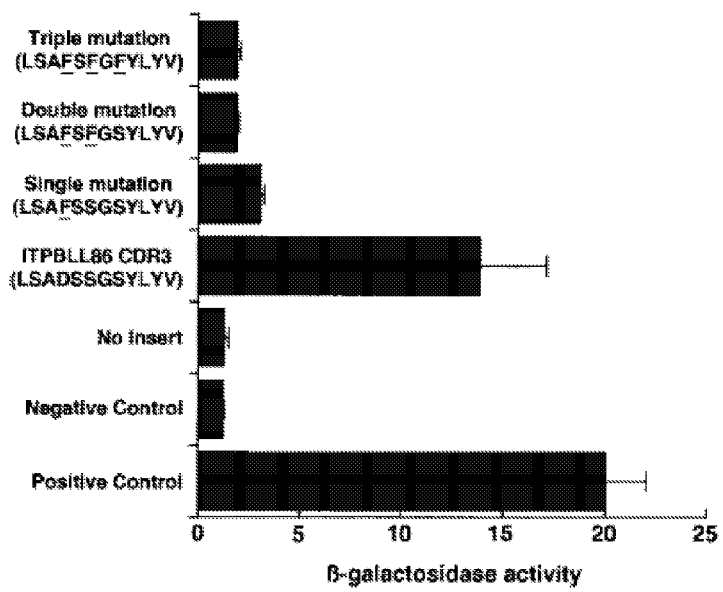
FIG. 6 shows the ability of the CDR3 sequence to form a loop structure is a critical determinant to binding of the Tamm-Horsfall protein. The histogram shows the CDR3 sequence of ITPBLL86 (LSADSSGSYLYV (SEQ ID NO:10)), which forms a loop structure, was mutated by substituting phenylalanines (underlined and bold) at one to three residues (LSAFSFGFYLYV (SEQ ID NO:29); (LSAFS FGSYLYV (SEQ ID NO:30); and (LSAFSSGSYLYV (SEQ ID NO:31)) within the sequence. Addition of these hydrophobic residues disrupted secondary structure. The wildtype sequence (LSADSSGSYLYV (SEQ ID NO:10)) interacted strongly with the Tamm-Horsfall protein, whereas, none of the mutated sequences interacted with the Tamm-Horsfall protein. N=7 experiments in each group.
Figure 7:
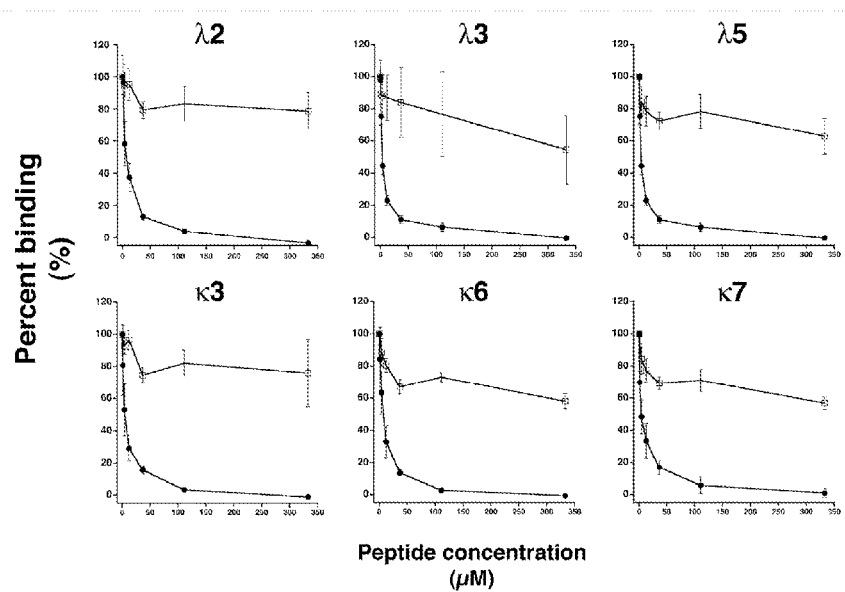
FIG. 7 shows multiple graphs of the effect of cyclized peptide on binding between human light chains and Tamm-Horsfall protein. The cyclized peptide (CLSADSSGSYLYVC) (SEQ ID NO:32), represented by closed circles, was a highly effective inhibitor that completely prevented the binding of Tamm-Horsfall protein to six different human light chains (λ2, 3 and 5 and κ3, 6, and 7). The control peptide (CLSAFSFGFYLYVC) (SEQ ID NO:33), represented by open squares, did not effectively inhibit binding of the light chains.

Mutation of the CDR3 sequence to disrupt the loop structure by substituting amino acid residues with phenylalanine confirmed that the secondary structure was an important determinant of binding (FIG. 6). The inhibitory capability of cyclized experimental (CLSADSSGSYLYVC (SEQ ID NO:32)) and control (CLSAFSFGFYLYVC (SEQ ID NO:33)) peptides were then compared in a competitive ELISA assay. The experimental peptide served as a very efficient inhibitor of the binding interactions between the human Tamm-Horsfall protein and six different human immunoglobulin light chains (FIG. 7).

Example 2

In Vivo Studies to Determine Peptides Capable of Inhibiting Light Chain Immunoglobulins Binding with Tamm Horsfall Protein A competitor peptide that mimics the CDR3 domain and binds to the Tamm-Horsfall protein with sufficiently high affinity to function in vivo was designed. The strength of binding, as indicated by the low $IC_{50}$, shows the peptide effectively competes with any immunoglobulin light chain for binding to Tamm-Horsfall protein. Cyclization of the peptide by addition of cysteine residues increased its affinity for Tamm-Horsfall protein.

The competitor peptides, SEQ ID NO:1 and SEQ ID NO:2, have been used in a rat model of cast nephropathy, which employed administration of human kappa and lambda light chains. The competitor peptides prevented cast formation and acute renal failure and improved renal function (Tables 3 and 4). Rats were injected intraperitoneally with 40 mg of cyclized competitor peptide, SEQ ID NO:2 (pep), or vehicle alone (veh) just prior to intraperitoneal injection of 100 mg of human kappa or lambda light chain purified from patients who had multiple myeloma and kidney damage. On the following day, rats also received an additional injection of competitor peptides, SEQ ID NO:1 (20 mg) or vehicle. Rats were examined three days after the initial injection.

TABLE 3

Competitor peptide prevented acute kidney injury from cast nephropathy.

| Group | Initial Wt (g) | Final Wt (g) | Wt Change (g) | Final BUN (mg/dl) | Final Serum Creatine (mg/dl) | Urine Flow Rate (μl/min per 100 g BW) | Final Ccr (μl/min per 100 g BW) |
|---|---|---|---|---|---|---|---|
| +Pep | 79 ± 2 | 86 ± 3 | 7 ± 2 | 15 ± 5 | 0.39 ± 0.03 | 1.9 ± 0.1 | 299 ± 58 |
| +Veh | 74 ± 2 | 67 ± 3 | −7 ± 2 | 47 ± 7 | 2.385 ± 0.2 | 0.09 ± 0.04 | 4 ± 2 |
| P Value | 0.231 | 0.008 | 0.01 | 0.02 | 0.0003 | <0.0001 | 0.007 |

Wt: weight; g: grams; mg: milligrams; dl: deciliter; μl: microliter; min: minute; BW: body weight; Ccr: clearance of creatinine; Pep: peptide; Veh: Vehicle

TABLE 4

Effect of parenteral administration of competing peptide versus vehicle on renal function following administration of free light chains.

| Group | Initial Wt (g) | Final Wt (g) | Wt change (g) | Final BUN (mg/dl) | Final Serum Creatinine (mg/dl) | Urine Flow Rate (μl/min per 100 g BW) | Final Ccr (μl/min per 100 g BW) |
|---|---|---|---|---|---|---|---|
| | | | | κ light chain | | | |
| +Pep | 79 ± 2 | 86 ± 3 | 7 ± 2 | 15 ± 5 | 0.39 ± 0.03 | 1.9 ± 0.1 | 264 ± 46 |
| +Veh | 74 ± 2 | 67 ± 3 | −7 ± 2 | 47 ± 7 | 2.38 ± 0.16 | 0.09 ± 0.04 | 7 ± 4 |
| P value | 0.231 | 0.008 | 0.01 | 0.02 | 0.0003 | <0.0001 | 0.005 |
| | | | | λ light chain | | | |
| +Pep | 130 ± 3 | 150 ± 4 | 18 ± 4 | 13 ± 2 | 0.46 ± 0.02 | 1.5 ± 0.4 | 77 ± 10 |
| +Veh | 130 ± 1 | 146 ± 2 | 8 ± 2 | 52 ± 5 | 1.30 ± 0.07 | 2.3 ± 0.7 | 29 ± 8 |
| P value | 0.811 | 0.361 | 0.098 | 0.003 | 0.0003 | 0.355 | 0.020 |

What is claimed is:

1. An isolated polypeptide consisting essentially of a QSYDNTLSGSYVF (SEQ ID NO:1) amino acid sequence or a LSADSSGSYLYVF (SEQ ID NO:2) amino acid sequence.

2. The polypeptide of claim 1, wherein the polypeptide is cyclized.

3. The polypeptide of claim 2, wherein the polypeptide further comprises a first cysteine residue at a carboxy-terminal end and a second cysteine residue at an amino-terminal end of the polypeptide.

4. A method of treating cast nephropathy in a subject, the method comprising:
(a) identifying a subject with or at risk of developing cast nephropathy; and
(b) administering to the subject a composition that inhibits the binding of a light chain immunoglobulin to a Tamm-Horsfall protein (THP), wherein the composition comprises the polypeptide of claim 1.

* * * * *